United States Patent [19]
Estey

[11] 3,939,713
[45] Feb. 24, 1976

[54] SEPTUM MOUNTING AND SHIELDING ASSEMBLY FOR SAMPLE INJECTION IN AN ANALYTICAL INSTRUMENT

[75] Inventor: Willard E. Estey, Ridgefield, Conn.

[73] Assignee: The Perkin-Elmer Corporation, Norwalk, Conn.

[22] Filed: Feb. 28, 1975

[21] Appl. No.: 554,280

[52] U.S. Cl. ............................................. 73/422 GC
[51] Int. Cl.[2] .......................................... G01N 1/00
[58] Field of Search ....................... 73/422 GC, 23.1

[56] References Cited
UNITED STATES PATENTS

| | | | |
|---|---|---|---|
| 3,564,925 | 2/1971 | Divelbliss | 73/422 GC |
| 3,672,226 | 6/1972 | Reid | 73/422 GC |

*Primary Examiner*—S. Clement Swisher
*Attorney, Agent, or Firm*—S. A. Giarratana; F. L. Masselle; J. K. Conant

[57] ABSTRACT

Disclosed is a septum-mounting and shielding assembly for a sample injector of the type utilized with gas chromatographs. The arrangement comprises an adapter flange designed for mounting on the inlet end of the sample injector block and containing a small diameter aperture through which a sample injection probe such as a hypodermic needle can be inserted. A septum holder is mounted for rotation relative to the adapter flange member about an axis eccentric to the aperture in the adapter flange. The septum holder contains a small diameter aperture which is eccentric relative to the axis of rotation, the degree of eccentricity being the same as that between the aperture and the adapter flange and the axis of rotation. Consequently, the two apertures are in registration in only one relative angular position of the septum holder. A silicone rubber septum is mounted in the septum holder coaxially with the aperture therein. When the apertures are aligned, the septum can be pierced with the injection probe which passes through the aligned apertures into the injector block; in other angular positions, the septum holder occludes the aperture in the adapter flange to prevent entry into the injector block of volatile components which might be out-gassed from the septum.

9 Claims, 2 Drawing Figures 3,939,713

SEPTUM MOUNTING AND SHIELDING ASSEMBLY FOR SAMPLE INJECTION IN AN ANALYTICAL INSTRUMENT

BACKGROUND OF THE INVENTION

Field of the Invention

This invention relates generally to sample injectors for analytical instruments such as gas chromatographs and, more particularly, to an arrangement for mounting and shielding the septum from exposure to the interior of the sample injector. In certain analytical instruments such as gas chromatographs, it is necessary to introduce a sometimes minute quantity of a sample to be analyzed by injecting it from a sample probe, customarily a hypodermic syringe, into a flowing stream of gas. The gas, carrying the injected sample, then passes through the chromatographic separation column and the effluent gas passed to a detector all in a manner well known in the art. A septum, most commonly a membrane of a physically permeable self-sealing material such as silicone rubber seals the entrance port of the injector block. The sample is introduced by piercing the septum with the injection probe, the puncture sealing itself when the probe is withdrawn.

It has long been recognized that it is desirable to interpose between the inner surface of the septum and the interior of the injector block a shield of inert material in order to prevent what is known as "septum bleed". This term refers to the tendency of the septum material, albeit relatively inert, to outgas or exhaust volatile components which are either constituents of the septum material itself or comprise analytical samples absorbed during a prior use of the injector.

With the development in recent years of improved detectors of extremely high sensitivity, the problem of septum bleed has become increasingly troublesome and a variety of remedies have been employed to cope with the problem. The basic approach common to these remedies is the use of a septum shield, which, in its simplest form as shown in U.S. Pat. No. 3,581,573 (FIG. 2) is a disc of inert material which overlies the face of the septum exposed to the interior of the injector block. The probe needle, when inserted, pierces both the septum and the shield; when withdrawn only that relatively small area of the septum which is in registration with the puncture hole in the shield is exposed to the interior of the injector block.

Another form of septum shield, shown in the aforementioned patent as well as in U.S. Pat. No. 3,635,093, employs a strip of shielding material disposed in sliding contact with the inner face of the septum. The ends of the strip are accessible from the exterior of the injection block so that, after the probe has been inserted and withdrawn, the puncture made in the shielding material can be moved out of registration with the septum which is then completely shielded from the interior of the injector block.

Both of these approaches to the problem of septum bleed have shortcomings: in one instance, the former, complete shielding of the septum is not achieved; and in the latter, it has proven difficult if not impossible in practice to achieve a satisfactory seal with the movable strip of shield material. In this connection it should be borne in mind that the high temperatures and moderate pressures encountered greatly complicate the sealing problem.

Another disadvantage is that, in all forms of septum shields shown in the above-referenced patents, it is necessary to remove the shielding element in order to replace the septum which, of course, must be done quite frequently. And in some forms, where the shield is a disc of probe-penetrable material, it is necessary or at least good practice to replace the shield as well as the septum. If this is not done, the puncture hole in the shield becomes enlarged or the shield is punctured in different places and the end result in both cases is that a larger area of the septum is exposed to the interior of the injector.

It is the primary general object of the present invention to overcome or at least mitigate the shortcomings of prior art devices as pointed out above.

A specific object is the provision of an improved septum shield arrangement in which the septum is totally shielded from the interior of the injection block and in which the septum can be replaced without removing the shielding member.

A further object is the provision of an improved septum mounting and shielding arrangement in which it is unnecessary to replace the shield and which is tightly sealed against leakage.

SUMMARY OF THE INVENTION

To the attainment of the foregoing objects, the present invention contemplates a septum mounting and shielding assembly comprising a flange member having a planar face and containing a through bore perpendicular to that face as well as a septum holder including a cylindrical flange portion having a planar surface disposed in confronting relation with the planar face of the flange. An additional bore extends through the flange portion of the septum holder along an axis perpendicular to the planar surface thereof and eccentric with respect to the cylindrical axis of the flange portion. Means are provided for movably retaining the septum holder for rotation relative to the flange member about a cylindrical axis and with the cylindrical axis eccentric to the bore in the flange member by an amount substantially equal to the eccentricity between the cylindrical axis and the bore in the septum holder. Sealing means are provided between the confronting face of the flange member and the planar surface of the septum holder and surrounding the bores in both members.

DESCRIPTION OF THE PREFERRED EMBODIMENT

Figure 1:
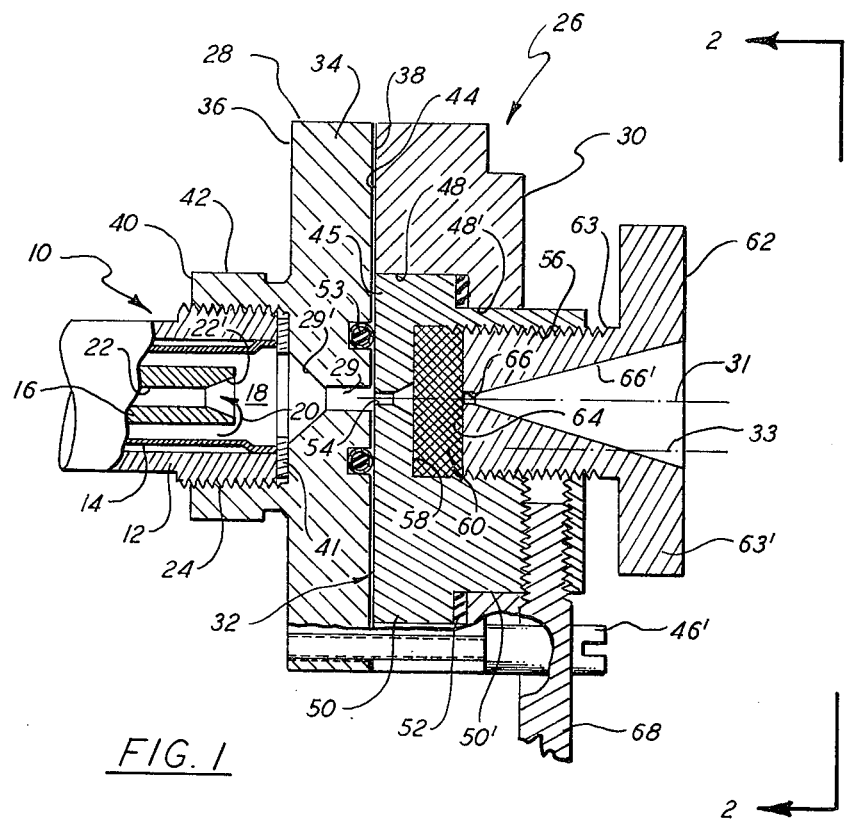
FIG. 1 is an axial sectional view showing a fragment of the inlet end of a sample injector block and including the septum mounting and shielding assembly of the present invention.

Referring to the drawings and first in particular to FIG. 1, there is illustrated in axial section and designated generally by reference numeral 10, the inlet end of an injector block of the type shown in U.S. Pat. No. 3,635,093 previously referred to. So much of the injector body 10 as is shown comprises a tubular injector body member 12 and, coaxially nested therein, a sleeve 14 and liner 16. In use, a carrier gas is introduced through an inlet, not shown, into the annular clearance space between the body member 12 and sleeve 14, from which it flows through passages, not shown, into the space between members 14 and 16 completely filling the volume designated by reference numeral 18 whence it flows as indicated by arrow 20 through and out of the opposite end of the bore 22 of tubular member 16, which is in flow communication with the separating column (not shown) of the chromatograph. Additional details as to the construction and operation of the injector block may be had by reference to the aforementioned U.S. Pat. No. 3,635,093.

The extreme end of the injector body member 12 is provided with external threads 24. In a manner that will be explained in greater detail as this description proceeds, a septum and septum shield-mounting assembly, designated in its entirety by reference numeral 26, is secured to the end of body member 12 by means of threads 24.

Mounting assembly 26 is made up of three principal components: an adapter flange member 28, a retaining bushing member 30 and a septum holder 32. Flange member 28 includes a flange portion 34 which, in the illustrated embodiment, is of circular outline and has generally circular or annular parallel planar faces 36 and 38. Coaxially projecting from planar face 36 is hollow cylindrical boss 40 internally threaded to engage the threads 24 on injector body 12. The exterior surface 42 of boss 40 is hexagonal or otherwise provided with tool-engaging flats to facilitate threaded installation and removal of adapter flange member 28. Adapter flange member 28 contains a through bore 29 which is in coaxial alignment with the bore 22 of liner member 16 when the adapter flange is mounted on injector body 12. At its end proximate the injector block, bore 29 terminates in a conical tapered portion 29'; the aligned bores coact to define a passage having an axis 31 into which the syringe-type sample-injection probe may be inserted into bore 22, which terminates in an outwardly flared portion 22' serving to guide and facilitate entry of the probe. An annular aluminum gasket 41 is provided between the end of injector body member 12 and adapter flange 34 to achieve a gas-tight seal at that location.

Figure 2:
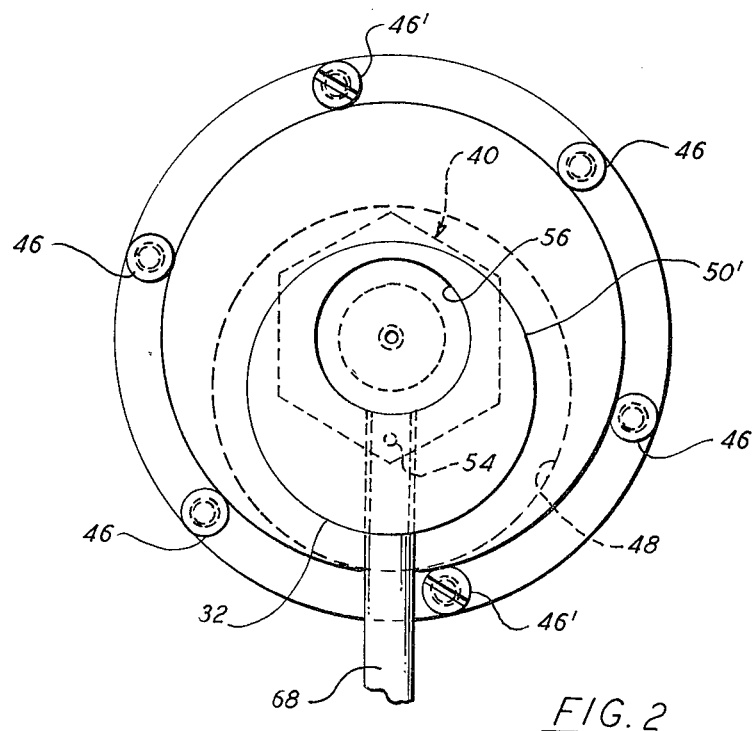
FIG. 2 is an end elevational view of FIG. 1, as viewed from line 2—2 of FIG. 1, with one member omitted in the interest of clarity of illustration.

Retaining bushing member 30 is of generally annular configuration and has one annular planar face 44 disposed in confronting relation to planar face 38 of adapter flange member 28. This relative disposition of the adapter flange member and retaining bushing member is established and maintained by means of a plurality of screw fasteners 46, 46' equiangularly spaced about the outer circumferences of the members (as best appears in FIG. 2) threaded into the flange portion 34.

Retainer member 30 contains a stepped internal bore having a large diameter portion 48 and a relatively smaller portion 48' coaxial with one another but having their common axis 33 eccentric with respect to axis 31 of bore 29 in the adapter flange member 28. Flange portion 34 of the adapter member and retaining bushing member 30 coact to define a chamber which rotatably receives and retains septum holder member 32. To this end, septum holder 32 has a relatively larger diameter cylindrical portion 50 received within the larger diameter bore 48 of the retainer member and a coaxial cylindrical portion 50' of relatively smaller diameter extending through the smaller diameter bore 48' of the retainer member and projecting axially outwardly therefrom. The larger and smaller diameter portions of septum holder 32 and corresponding bores of retaining bushing 30, coact to define confronting annular shoulders which provide seating surfaces for a bearing member such as a filled Teflon washer 52.

The confronting surfaces 38 and 45 of adpater flange member 28 and septum holder 32 are sealed by a Teflon encapsulated silicone O-ring 53 disposed in a groove concentric to bore 29 in the flange member. In this manner, a gas-tight seal is formed between septum holder 32 on one hand and the adpater member 28 on the other while permitting relative rotation.

At a point eccentric with respect to its axis of the large diameter portion 50, septum holder 32 is provided with a probe aperture in the form of a small bore 54 flaring outwardly in a direction away from injector block 12. Septum holder member 32 is provided with an internally-threaded counter bore 56 coaxial with but of much larger diameter than probe aperture bore 54. The junction of bores 54 and 56 forms a relatively wide annular seat 58 for a silicone rubber septum member 60 of discoid configuration.

A septum knob 62 has an externally-threaded cylindrical shank portion 63 and an enlarged head 63' to facilitate manual threaded insertion of the knob into counter-bore 56. The inner end of septum knob shank portion 63 has an annular face 64 which bears on and clamps septum 60 against annular shoulder 58. Inner face 64 contains a small bore 66 which extends a small fraction of the axial dimension of knob shank 63 and then flares outwardly to provide a conical guide surface 66' for directing a sample probe to the small diameter bore.

In the angular position shown in FIG. 1, small diameter bore 66 is coaxially aligned with bores 54 and 29 in the septum holder and adapter flange, respectively. As a result of the eccentricity of probe passage axis 31 with respect to the cylindrical axis 33 of septum holder member 32, rotation of the septum holder member by a significant amount from the position shown results in moving probe aperture 54 out of registration with bore 29 and outside the perimeter of Teflon encapsulated silicone O-ring seal 53. To facilitate this rotation, a radially-extending lever 68 is threaded into the small diameter portion 50' of septum holder 32. Of the ring of screws securing retainer member 30 to adapter flange 34 two, designated 46', are actually screw pins having cylindrical portions which project axially beyond the face of retaining bushing member 30 and thus function as abutments or stops which, by engagement with rotating lever 68, limit the rotation of septum holder 32 to two positions substantially 180° apart. In one position, which may be referred to as the "open" position, bores 66, 54, 29, and 22 are in registration permitting a probe to be inserted through septum 60 into liner member 16. When the sample has been injected and the probe withdrawn, rotating lever 68 is moved to the opposite or closed position in which bore 54 is outside the perimeter of the O-ring 53 (as shown in dotted line in FIG. 2) and thus the septum is completely shielded from the internal volume 18 of the injector block.

It will be noted in reference to FIG. 1 that septum 60 may be replaced by simply removing septum knob 62, removing the old septum, inserting a new septum and replacing the septum knob.

What is claimed is:

1. In a sample injector for analytical instruments in which a sample is introduced into the instrument by means of a probe which is thrust through a self-sealing septum, a septum mounting and shielding assembly comprising:

means defining a passage through which the probe may be inserted into communication with the instrument;

a septum holder member containing a bore aligned with and constituting a part of said passage;

and means mounting said septum holder member for rotary movement about an axis eccentric to said passage whereby rotation of said member selectively moves said bore into and out of registration with said passage.

2. The invention defined in claim 1, including means defining an outwardly open counterbore in said septum holder member of larger diameter than and coaxial with said first mentioned bore, the junction of said bores defining an annular shoulder for seating a discoid septum; and means removably disposed in said counterbore for retaining a septum in sealing engagement with said shoulder.

3. The invention as defined in claim 2 wherein said last-mentioned means contains a bore coaxially aligned with said first mentioned bore and constituting part of said passage.

4. The invention as defined in claim 3 including radial lever means secured to said septum holder for rotating same; and spaced abutment means defining a first limit position of rotation of said septum holder whereat said first-mentioned bore is aligned with said passage and a second limit position of rotation whereat said first-mentioned bore is out of registration with and sealed from communication with said passage.

5. In a sample injector for analytical instruments, a septum mounting and shielding assembly comprising:

a flange member having a planar face and containing a through bore perpendicular to said face;

septum-holder means including a septum-holder member with a cylindrical flange portion having a planar surface;

means defining a second bore extending through the flange portion of the septum-holder member along an axis perpendicular to said planar surface, and eccentric with respect to the cylindrical axis, of said flange portion;

means rotatably retaining said septum-holder member with the planar surface of its flange portion in confronting relation to the planar face of said flange member, for rotation relative thereto about said cylindrical axis and with the cylindrical axis eccentric to the first bore by an amount substantially equal to the eccentricity between the second bore and the cylindrical axis; and sealing means between said confronting face and surface and surrounding said first and second bores.

6. An arrangement according to claim 5 wherein said septum-holder means includes:

means defining a cylindrical cavity in said septum-holder member coaxial with, and of larger diameter than, said second bore, thus to create an annular shoulder at the conjunction of the bore and cavity; and means for replacably retaining a septum seated on said annular shoulder.

7. An arrangement according to claim 6 wherein said cavity is internally threaded and said septum-retaining means comprises an externally-threaded cylindrical member threadable into said cavity and containing a through conically-tapered axial bore having its apex directed inwardly into said cavity and terminating in a bore coaxial with and in spaced opposition to said second bore.

8. An arrangement according to claim 7 wherein said flange member is of generally discoid configuration and, on the face opposite said planar face, has a threaded hollow cylindrical boss coaxial with said first bore, adapting said flange member for threaded attachment to a sample injector.

9. An arrangement according to claim 8 wherein said septum-holder member has a second cylindrical portion which defines said cylindrical cavity, said second cylindrical portion being smaller than and coaxial with said cylindrical flange portion and wherein said septum-holder retaining means comprises a cup-shaped bushing having a stepped internal bore, the larger diameter segment of which rotatively receives the cylindrical flange portion of the septum-holder member and the smaller diameter segment of which defines with the larger diameter segment an annular shoulder coating with the annular shoulder defined by the cylindrical flange portion and second cylindrical portion of the septum-holder member to define an annular clearance space; washer means disposed in said annular clearance space; and fastener means detachably securing said septum-holder retaining means to said planar face of the flange member and urging said septum-holder member into sealing engagement with said sealing means.

* * * * *